(12) United States Patent
Soffiatti et al.

(10) Patent No.: US 10,463,498 B2
(45) Date of Patent: *Nov. 5, 2019

(54) CONSTRAINED PROSTHESIS FOR THE KNEE JOINT

(71) Applicant: TECRES S.p.A., Simmacampagna (Verona) (IT)

(72) Inventors: Renzo Soffiatti, Nogra (IT); Giovanni Faccioli, Monzambano (IT)

(73) Assignee: TECRES S.P.A., Sommacampagna (VR) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/513,684

(22) PCT Filed: Jun. 30, 2015

(86) PCT No.: PCT/IB2015/054924
§ 371 (c)(1),
(2) Date: Mar. 23, 2017

(87) PCT Pub. No.: WO2016/046654
PCT Pub. Date: Mar. 31, 2016

(65) Prior Publication Data
US 2017/0281354 A1    Oct. 5, 2017

(30) Foreign Application Priority Data
Sep. 23, 2014   (IT) .............................. VR2014A0232

(51) Int. Cl.
*A61F 2/38*   (2006.01)
*A61F 2/30*   (2006.01)

(52) U.S. Cl.
CPC ............ *A61F 2/3836* (2013.01); *A61F 2/384* (2013.01); *A61F 2/38* (2013.01); *A61F 2220/0041* (2013.01)

(58) Field of Classification Search
CPC .......... A61F 2/38; A61F 2/389; A61F 2/3859; A61F 2002/30604; A61F 2002/30934;
(Continued)

(56) References Cited

U.S. PATENT DOCUMENTS 3,765,033 A * 10/1973 Goldberg ................ A61F 2/384
  623/20.26
3,969,773 A    7/1976 Menschik
(Continued)

FOREIGN PATENT DOCUMENTS

| EP | 0406606 | 1/1991 |
| EP | 1132064 | 9/2001 |

(Continued)

*Primary Examiner* — Ann Schillinger
(74) *Attorney, Agent, or Firm* — Tutunjian & Bitetto, P.C.

(57) ABSTRACT

Constrained prosthesis for the knee joint including a femoral component, a tibial component and an intermediate component, wherein the femoral component is suitable for being constrained to an end of the femoral bone in proximity to the knee joint, wherein the tibial component is suitable for being constrained to an end of the tibial bone in proximity to the knee joint, the femoral component being suitable for coming into contact and being articulated with the tibial component, wherein the intermediate component is placed in use between the femoral component and the tibial component and wherein the constrained prosthesis comprises a first hinge and a second hinge adapted to rotatably constrain the femoral component to the tibial component.

5 Claims, 8 Drawing Sheets

(58) Field of Classification Search
CPC ............... A61F 2002/3863; A61F 2/64; A61F 2002/4205
See application file for complete search history.

(56) References Cited

U.S. PATENT DOCUMENTS

| | | |
|---|---|---|
| 5,123,928 A | 6/1992 | Moser |
| 10,092,407 B2 * | 10/2018 | Faccioli ................. A61F 2/385 |

FOREIGN PATENT DOCUMENTS

| | | |
|---|---|---|
| FR | 2241284 | 3/1975 |
| GB | 2129306 | 5/1984 |

\* cited by examiner

CONSTRAINED PROSTHESIS FOR THE KNEE JOINT

TECHNICAL FIELD OF THE INVENTION

The present invention relates to a constrained prosthesis which can be employed for knee prosthesis revision, for example following an infection. In this case, the constrained prosthesis according to the present invention is a revision prosthesis.

STATE OF THE PRIOR ART

Generally, the knee joint is formed by a pair of condyles placed in the distal portion of the femur. The lower surface of the condyles rests and slides/rolls on corresponding surfaces of the tibial plateau, shaped in a manner corresponding to the lower surface of the condyles themselves.

The femur and the tibia are then connected by ligaments which confer stability to the joint.

In the field of joint prosthesis implantology it is known that such devices may have to be removed for different reasons, in particular, due to local infections of the joint arising after the implantation of the prosthesis itself.

In this case, after removing the first prosthesis, it is necessary to treat the joint seat with suitable antibiotic medicaments, before being able to implant the new prosthesis.

During the period of treatment it is essential to maintain the joint space necessary for the implant of a new prosthesis, so as to avoid tissue shortening, joint atrophy and loss of muscle tone.

This technique is known as "two-step implantation" of joint prostheses.

Sometimes, a second infection may arise, therefore also the second implanted prosthesis must be replaced, after a suitable treatment period, with a third prosthesis.

Sometimes, when the knee joint is particularly weak or when, for surgical needs, the amount of bone removed is considerable, it may be necessary to implant a constrained device.

Such constrained device comprises a femoral component and a tibial component which are mechanically connected to each other by means of a hinge structure.

Constrained prostheses of the known type generally comprise a hinge structure provided with a locking pin, which in use is inserted and locked in the tibial component of the prosthesis itself.

The hinge component, thus rigidly constrained to the tibial component, is then rotatably connected to the femoral component.

Temporary joint spacers for the knee are also present on the market, generally made of bone cement, able to perform the function set forth above.

Some of these are manually obtained by the surgeon directly during the surgical implantation of the spacer itself, by suitably shaping the material of which the same is made, depending on the size and shape of the implant site.

Spacers for the knee joint are also available on the market that are pre-formed and, therefore, directly ready for implantation. Such spacers generally have two articular condyles on the femoral component that rest and slide or rotate on a corresponding surface, placed on the tibial component.

SUMMARY OF THE INVENTION

An object of the present invention is to improve the state of the prior art.

A further object of the present invention is to provide a final prosthesis, so-called "revision prosthesis", for the knee joint, after revision of a previous prosthesis.

Still a further object of the present invention is to provide a constrained prosthesis that is pre-formed and, at the same time, adaptable to the actual conditions of the knee joint in which the same is to be implanted, also considering the amount of excised bone tissue following the removal of the infected joint prosthesis or the weakness of the ligaments present in the joint to be treated.

A further object of the present invention is to provide a constrained prosthesis that ensures high mobility and stability of the joint itself.

A still further object of the present invention is to provide a constrained prosthesis that mechanically constrains in an articulated manner the femoral component to the tibial component and thus, accordingly, the femoral bone to the tibial bone, allowing the roto-translational articulation thereof.

A still further object of the present invention is to provide a constrained prosthesis that ensures a good quality of life for the patient following the implantation of the device itself.

According to an aspect of the present invention, a constrained prosthesis for the knee joint according to an embodiment of the present specification is provided.

The present invention further relates to a method for assembling a constrained prosthesis for the knee joint according to an embodiment of the present specification.

The present specification refers to preferred and advantageous embodiments of the invention.

BRIEF DESCRIPTION OF THE DRAWINGS

Further characteristics and advantages of the present invention will be clearer from the detailed description of a preferred but not exclusive embodiment of a constrained prosthesis for the knee joint, illustrated by way of an indicative, but not limitative, example in the accompanying drawings, in which.

DETAILED DESCRIPTION

As known, articular surfaces in the knee joint are represented by femoral condyles and related tibial support bases.

The articular surface of the femur, consisting of the lower surface of the two condyles is smooth and 'U'-shaped, it is articulated with the tibial plateau, that is the upper surface of the proximal epiphysis of the tibia.

With reference to the enclosed figures, 1 generally indicates a constrained prosthesis for the knee joint.

The need to use a constrained prosthesis may derive from the fact that the ligaments of the patient to be treated may be particularly weak, or the resection of the bone may be too large, and therefore there is a need to insert a constrained prosthesis having an inherent stability.

The constrained prosthesis 1 according to the present invention may be used for example as a first implant or second or third implant, to be inserted following revision, if the already exposed reasons of joint weakness or lack of adequate bone support exist.

Such constrained prosthesis 1 comprises a femoral component 2 and a tibial component 3.

The femoral component 2 is adapted to be constrained to the end of the femoral bone in proximity to the knee joint while the tibial component 3 is adapted to be constrained to the end of the tibial bone at the knee joint.

In one version of the invention, only a femoral component 2 and a tibial component 3 are present, constrained to each other, while patellar components are not present, since one of the purposes of the constrained prosthesis 1 is to reduce the complexity of the implant.

Instead, in an alternative version, the patellar component may be present.

The femoral component 2 comprises a shape that broadly reproduces the condylar articulation surfaces of the femur.

Figure 1:
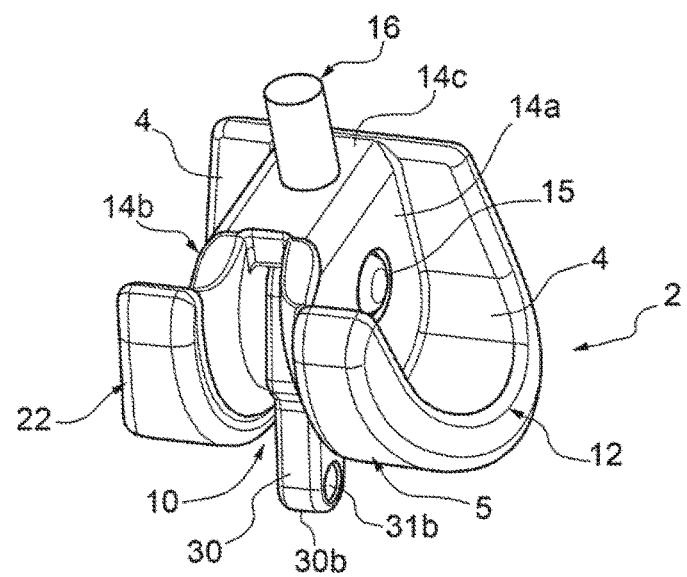
FIG. 1 is a perspective rear-side view of a femoral component of the constrained prosthesis according to the present invention.
Figure 7:
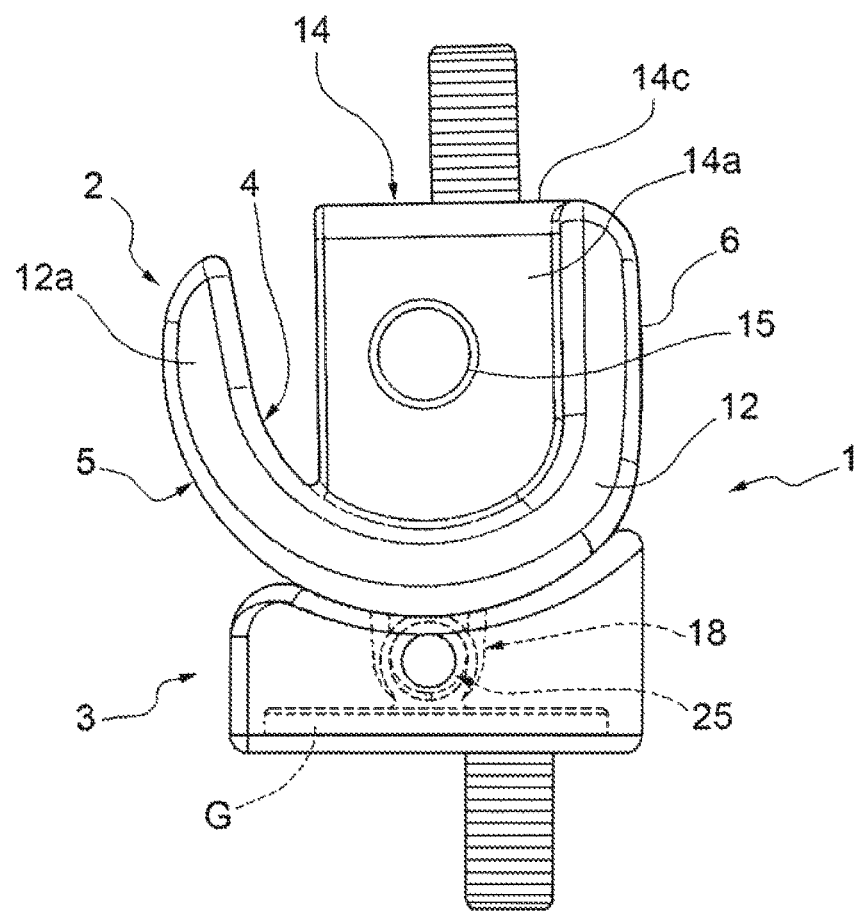
FIG. 7 is a side view of the assembled constrained prosthesis of FIG. 5.

In particular, the femoral component 2 has, as is visible in the assembled side FIG. 7 and in the not assembled perspective FIG. 1, a substantially 'U'-shaped cross-section according to a plane parallel to the sagittal plane of the human body, comprising an inner surface 4, substantially concave, in contact with the bone seat, and an outer surface 5, substantially convex, suitable for coming into contact with the tibial component 3.

Specifically, the femoral component 2 comprises two condylar portions 12, 22, a first condylar portion 12 placed laterally and a second condylar portion 22 placed medially with respect to the sagittal plane of the human body, each having a shape similar to that of the condyles of the knee.

The condylar portions 12, 22 have in turn a substantially 'U'-shaped cross-section according to a plane parallel to the sagittal plane of the human body, comprising the inner surface 4, substantially concave, in contact with the bone seat, and the outer surface 5, substantially convex, suitable for articulating and coming into contact with the tibial component 3.

The condylar portions 12, 22, in their portion that in use is anterior of the constrained prosthesis 1 according to the present invention, converge towards each other and, in one version of the invention, are joined to form a patellar portion or surface 6, suitable for coming into contact with the patella or being substantially arranged in the area in which it is usually located from the anatomical point of view.

In an alternative version of the invention, the condylar portions 12, 22, in their portion that in use is anterior of the constrained prosthesis 1 according to the present invention, converge towards each other but are not joined and remain separate, forming two patellar portions or surfaces (not illustrated).

As visible in the side FIG. 7, the patellar portion or surface 6 is substantially parallel to the frontal plane of the human body.

The outer surface 5, in such patellar portion or surface 6, is therefore substantially planar.

The condylar portions 12, 22, in their portion that in use is posterior of the constrained prosthetic device 1 according to the present invention, comprise a first and a second posterior portion 12a, 22a, separated from each other by an intercondylar space 10.

The femoral component 2 comprises a box-like element 14, placed on the inner surface 4.

The box-like element 14 has two side walls 14a, 14b and a connecting wall 14c, to which it connects and joins the side walls 14a and 14b.

The box-like element 14 has a substantially inverted 'U'-shaped cross section according to a plane parallel to the frontal plane of the human body.

Between the side walls 14a, 14b and the connecting wall 14c a seat or cavity 140 is comprised.

The free peripheral edges of the side walls 14a, 14b are in contact with and connected to the inner surface 4 of the femoral component 2.

In particular, the side walls 14a, 14b are placed at the inner peripheral edges of the condylar portions 12, 22, so as to enclose the intercondylar space 10.

In this way, the seat or cavity 140 of the box-like element 14 corresponds to the intercondylar space 10.

Possibly, also one of the two free sides of the connecting portion 14c may be in contact and/or connected to the inner surface 4 of the femoral component 4.

At the connecting wall 14c, a cylindrical protrusion or shank 16 may be present, possibly threaded, for connecting, fixing and centering or orienting the femoral component 2 at the bone end of the femoral bone F.

On each side wall 14a, 14b of the box-like element 14a through hole 15 is present; the holes 15 present on the two side walls 14a, 14b are aligned along a same axis, so-called rotation axis or rotating constraint.

In a simplified version of the invention, this axis is horizontal, considering the arrangement in space of the femoral component 2 in use.

A pin 150 may be inserted into such through holes 15, as will be better described below in this discussion.

The constrained prosthesis 1 according to the present invention comprises, as mentioned, a tibial component 3.

The tibial component 3 comprises a tibial plateau 20 and, possibly, a cylindrical protrusion or shank 16, possibly threaded, for connecting, fixing and centering or orienting the tibial component 3 to the bone end of the tibial bone P.

The femoral component 2 described above rests, rolls and/or slides and is articulated on the tibial plateau 20.

The tibial plateau 20 comprises two condylar articular bases 13, 23, corresponding to the condylar portions 12, 22.

The cylindrical protrusion or shank 16 extends from the face of the tibial component 3 opposite that having the two condylar articular bases 13, 23.

The condylar articular bases 13, 23 are substantially concave and have a radius of curvature R2.

The condylar portions 12, 22, in particular the posterior portions 12a, 22a thereof, and/or the intermediate ones, have a radius of curvature R1.

As is visible in FIG. 7, the radius of curvature R1 of the condylar portions 12, 22 and the radius of curvature R2 of the condylar articular bases 13, 23 substantially correspond to each other.

In one version of the invention, R1=[R2−(R2× (0.05±0.5)], therefore, R1 is smaller than R2.

The tibial component 3 further comprises, between the condylar articular bases 13, 23, an intercondylar protuberance 24.

Such intercondylar protuberance 24 is extended vertically upwards, considering the tibial component 3 placed on the knee.

The intercondylar protuberance 24, in use, is suitable for being inserted in the intercondylar space 10 of the femoral component 2, so as to create a guided articulation between the femoral component 2 and the tibial component 3.

Figure 2:
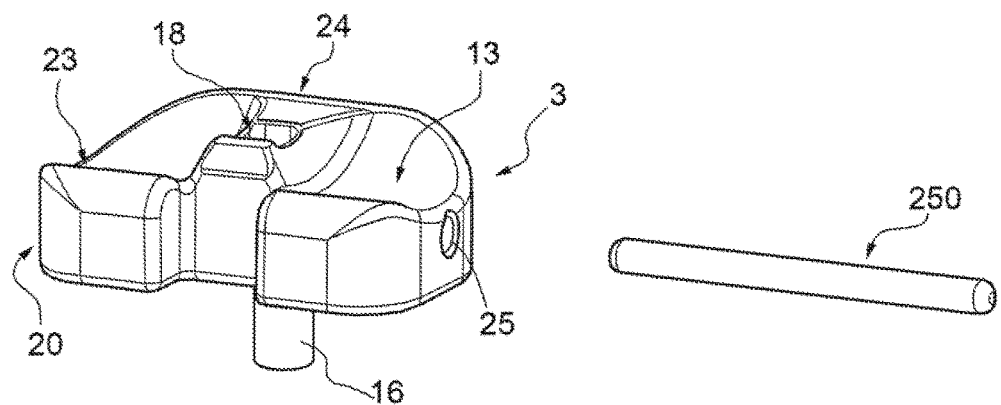
FIG. 2 is a perspective rear-side view of a tibial component of the constrained prosthesis according to the present invention.
Figure 3:
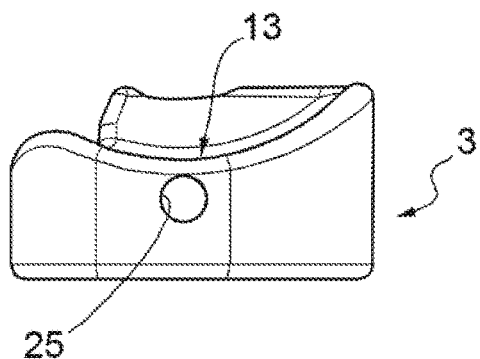
FIG. 3 is a side view of part of the tibial component of FIG. 2.
Figure 4:
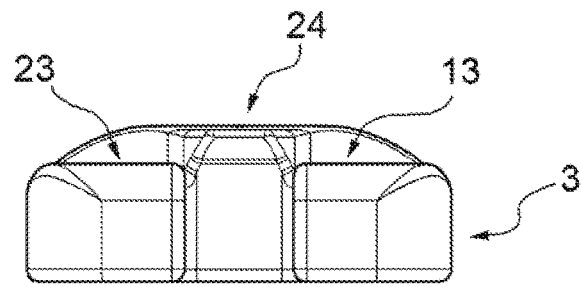
FIG. 4 is a rear view of part of the tibial component of FIGS. 2 and 3.

Observing for example FIGS. 2 and 3 that illustrate the tibial component 3, the latter has a transverse development, in use from right to left, of bigger size than the sagittal development of the same, that is in use from front to back with respect to the human body.

The two condylar articular bases 13, 23 are placed at the lateral and medial ends of the tibial component 3, considering the transverse development of the latter, while the intercondylar protuberance 24 is placed at the center of the tibial component 3, between the aforesaid condylar articular bases 13, 23.

The intercondylar protuberance 24 has a parallel development with respect to the sagittal plane of the human body, considering its largest dimension.

Considering the tibial component 3 in its position of use, it has a peripheral surface comprising a medial side, a lateral side, a front side and a rear side.

The medial side and the lateral side have a parallel development with respect to the sagittal plane of the human body while the front and rear sides are parallel to the frontal plane of the human body.

The intercondylar protuberance 24 has an opening or recess 18 with substantially parallel development with respect to the longitudinal axis of the human body.

The opening or recess 18 is extended inside the tibial component 3 for a certain length T.

The length T, according to a preferred version of the invention, is smaller than the height H of the intercondylar protuberance 24, so that the opening or recess 18 only affects the upper face, in use, of the tibial component 3, where the condylar articular bases 13, 23 are present. In this manner, the bone cement used to fix the tibial component 3 to the tibial end cannot penetrate into the opening or recess 18, for the reasons which will become apparent hereinafter.

The tibial component 3 further comprises a hole 25.

The hole 25 has rectilinear and transversal or horizontal development with respect to the tibial component 3.

The hole 25 affects at least one side, medial or lateral, of the tibial component 3.

In one version of the invention, the hole 25 is a though hole, that is it affects both the medial and the lateral side of the tibial component 3.

The hole 25 intersects the opening or recess 18 of the intercondylar protrusion 24.

A pin 250 may be inserted in this hole 25, as will be better described later in this discussion. The pin 250, therefore, once inserted in the hole 25, also passes through the opening or recess 18.

The constrained prosthesis 1 according to the present invention further comprises an intermediate component 30, having for example a rod-like shape. The intermediate component 30 is a connection element, suitable for rotatably connecting the femoral component 2 and the tibial component 3, in order to obtain a rotary motion and/or translational motion between the same during the knee articulation.

The intermediate component 30 is placed in use between the femoral component 2 and the tibial component 3.

The intermediate component 30 has an elongated shape; such shape may be substantially rectangular or bilobed or with chamfered edges. The intermediate component 30 may also have other shapes suitable for allowing it to perform the function that will be described hereinafter.

The intermediate component 30 has its largest dimension substantially aligned with the longitudinal axis of the human body.

In particular, the intermediate component 30 has a proximal end 30a and a distal end 30b.

The proximal end 30a is placed at the femoral component 2; in particular, the proximal end 30a is suitable for being inserted into the intercondylar space 10 determined by the inner area of the box-like element 14.

The distal end 30b, instead, is placed at the tibial component 3; in particular, the proximal end 30b is adapted to be inserted into the opening or recess 18 of the intercondylar protuberance 24 of the tibial component 3.

The dimensions of the opening or recess 18 are greater than the overall dimensions of the distal end 30b of the intermediate component 30, so as to have a play between the two and so that the latter can thus move inside the opening or recess 18 according to a sagittal and/or transversal direction with respect to the human body.

The intermediate component 30 comprises a through hole 31a, at the proximal end 30a and a through hole 31b, at the distal end 30b.

The constrained prosthesis 1 according to the present invention comprises two hinges 32a and 32b, the first hinge 32a placed at the proximal end 30a of the intermediate component 30 and the second hinge 32b at the distal end 30b of the same.

The two hinges 32a, 32b are adapted to rotatably constrain the femoral component 2 to the tibial component 3.

The two hinges 32a, 32b consist of the pin 150, housed in the holes 31a and 15, provided that the hole 31a is aligned with the through holes 15 of the box-like element 14, and of the pin 250, housed in the holes 31b and 15, provided that the hole 31b is aligned with the hole 25 of the tibial component 3, respectively.

The hinge 32b, therefore, is placed inside the opening or recess 18 of the tibial component 3.

Specifically, the hinges 32a, 32b each constitute a constraint that only allows the femoral component 2 and the tibial component 3 to rotate, eliminating any possible mutual translation.

The hinge connects two solid objects, normally allowing only a limited angle of rotation between the same. Two objects connected by an ideal hinge rotate with respect to each other around a fixed rotation axis (the geometrical axis of the hinge).

The femoral component 2 and the tibial component 3 are therefore rotatably constrained to each other by means of the intermediate component 30 and to the hinges 32a and 32b.

The constrained prosthesis 1 according to the present invention, therefore, allows both rolling and limited sliding of the femoral component 2 on the tibial component 3, due to the intermediate component 30 being capable of limited oscillation, having the hinge 32b and the pin 250 as a fulcrum, inside the opening or recess 18.

Figure 8:
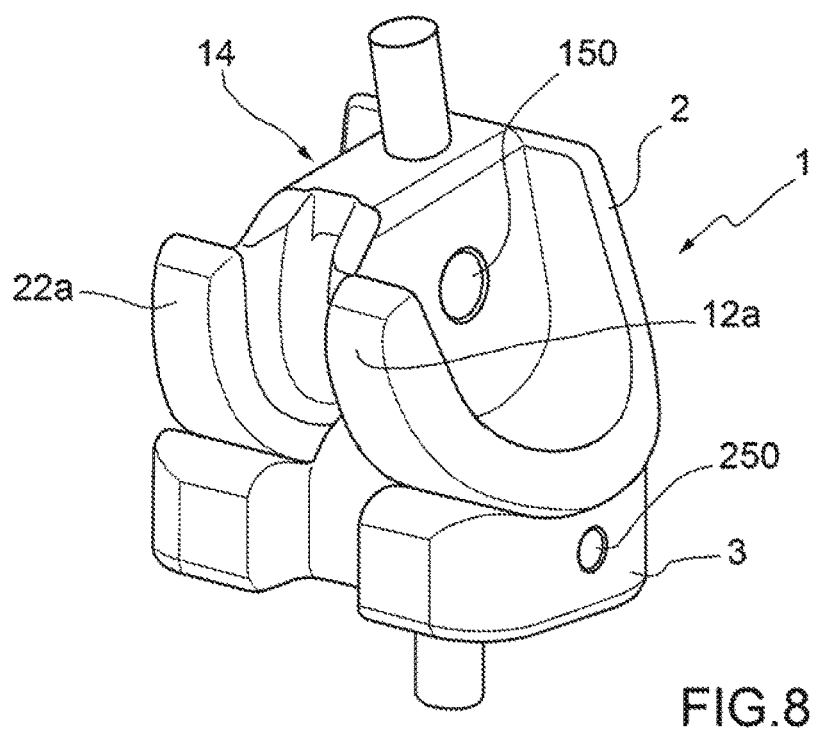
FIGS. 8 and 9 are perspective rear-side views of the assembled constrained prosthesis according to the present invention in which the femoral component and the tibial component are articulated with each other according to a first and a second angular arrangement.
Figure 9:
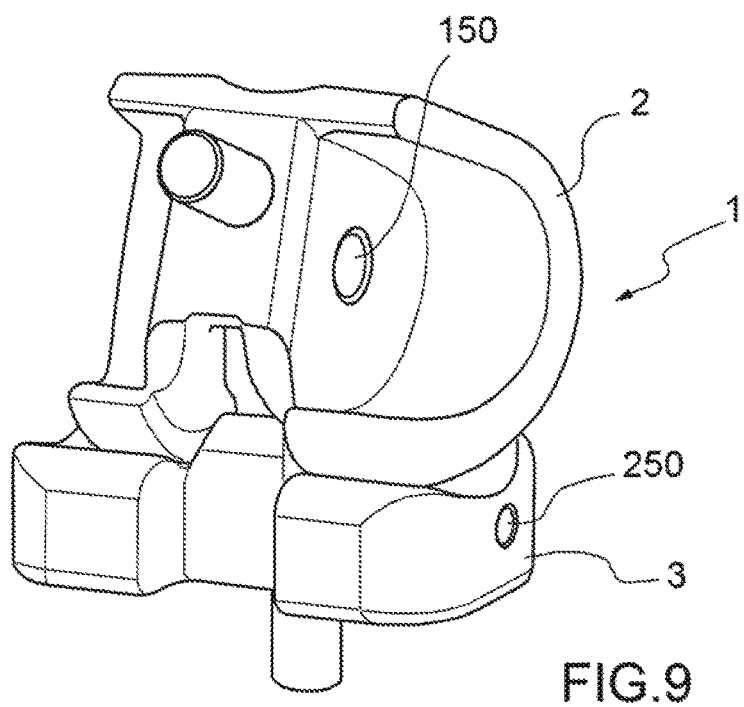

In this manner, the center of rotation of the femoral component 2 on the tibial component 3—that corresponds to the hinge 32a and to the pin 150, does not remain, during the knee articulation (two positions of which are illustrated in the FIGS. 8 and 9), always in the same position but it translates in a limited manner, depending on the width of the oscillation of the intermediate component 30, as previously described.

The intermediate component 30 therefore performs the function of constraint between the parts corresponding to the femoral component 2 and to the tibial component 3 and thus between the respective femoral F and tibial P bone portions.

Moreover, in the case in which the bone stumps on which the constrained prosthesis 1 according to the present invention is implanted are very small, it is possible to provide additional shanks 40 or rings or thicknesses, able to elongate such bone ends and bring them closer to their original position.

Figure 10:
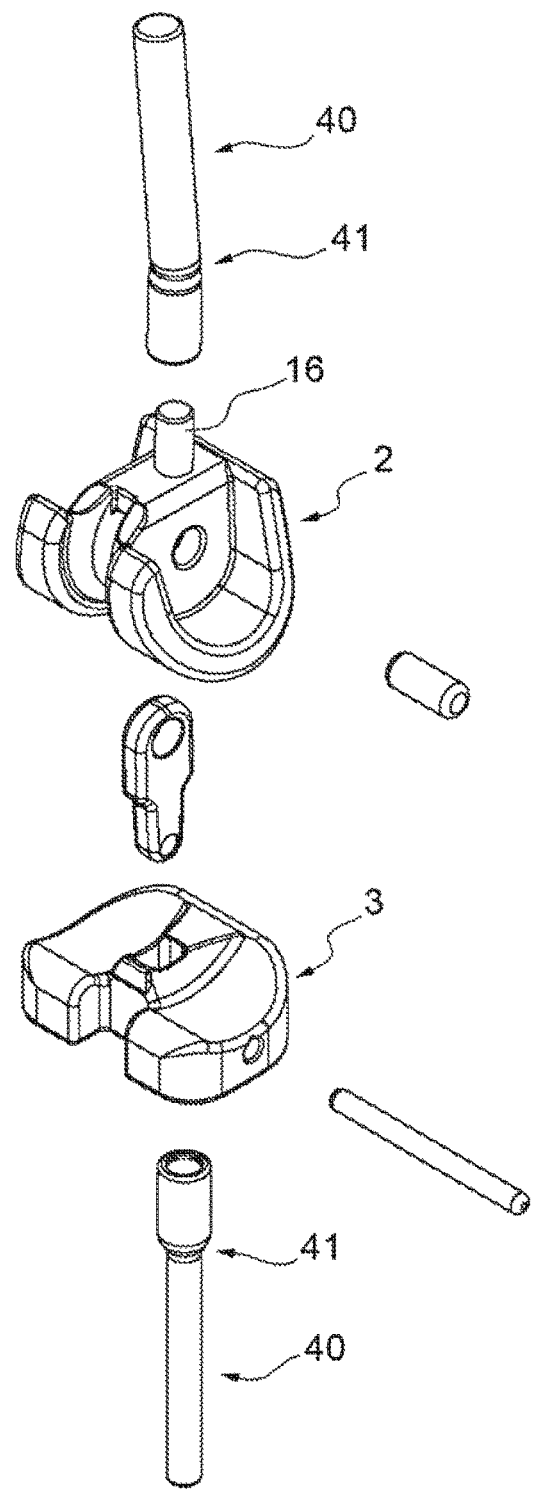
FIG. 10 is an exploded view of a version of the constrained prosthesis according to the present invention.
Figure 11:
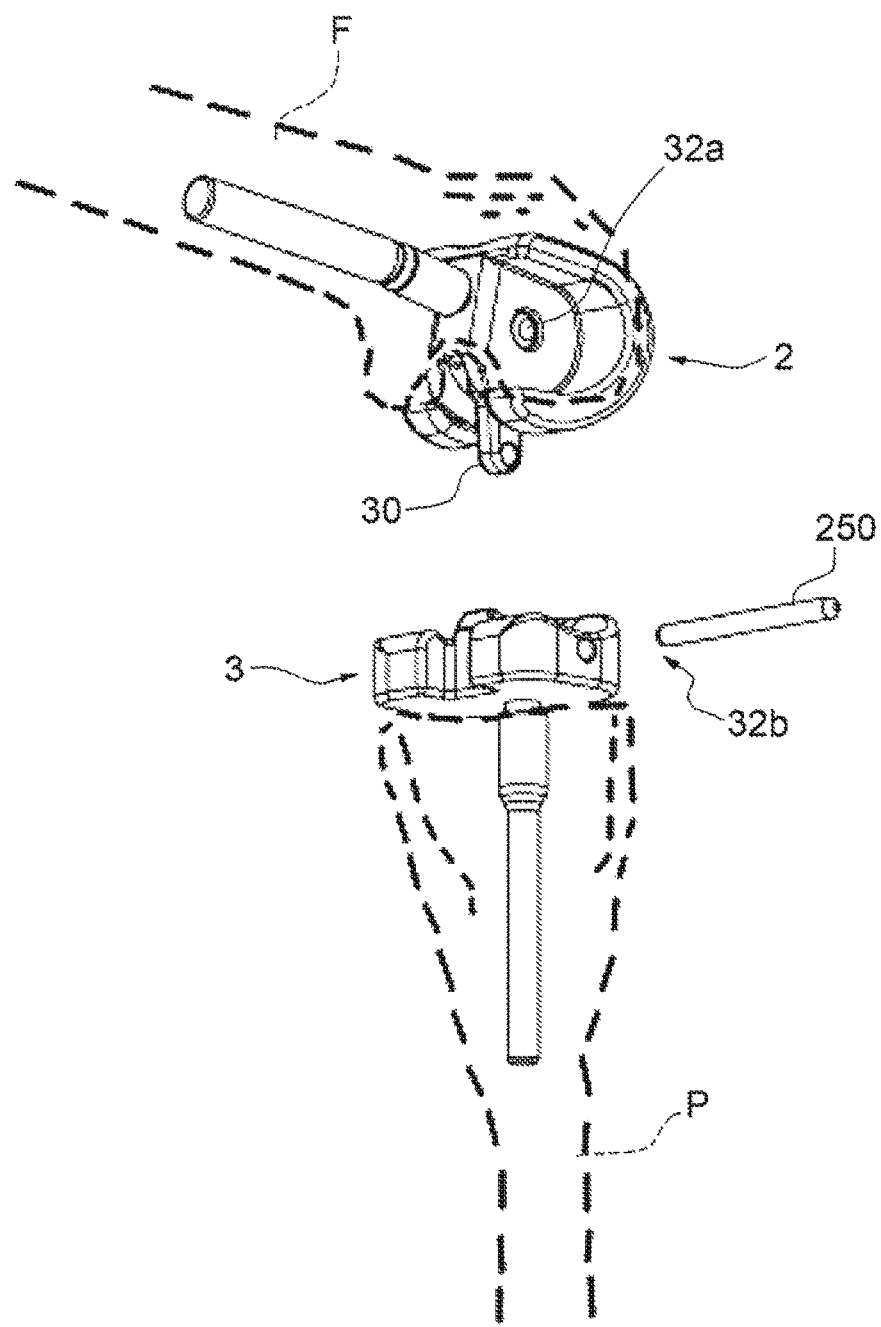
FIG. 11 is a perspective view of the constrained prosthesis according to the present invention associated with the respective bone portions (dashed lines)
Figure 12:
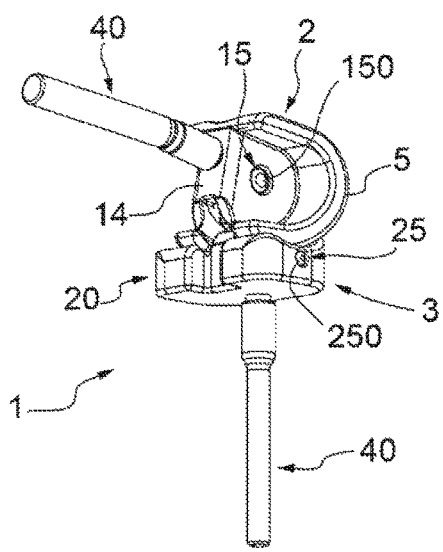
FIG. 12 is a side perspective view of the constrained prosthesis according to the present invention in a first operating position.

In particular, as is visible in FIG. 10, the additional shanks 40 may be connected or constrained, if necessary, to the cylindrical protrusion or shank 16 present in the femoral component 2 and/or in the tibial component 3. Such additional shanks 40 may, in one version of the invention, be connected by means of a removable threaded connection to the cylindrical protrusion or shank 16.

The additional shanks 40, in one version of the invention, may have a ball joint 41 or in general rotating means, so as to allow the rotation in all directions and thus the orientation of the second additional shank 40 portion opposite the first additional shank 40 portion, the latter being placed at the cylindrical protrusion or shank 16.

The cylindrical protrusion or shank 16 and/or the additional shanks 40, in particular their first portion, may be provided tilted, for example by 5°, in order to facilitate the orientation thereof with respect to the femoral F and/or tibial P bone of the patient.

The constrained prosthesis 1, according to a non-limiting version of the invention, is assembled according to the following method.

The intermediate component 30 is associated in a constrained manner to the femoral component 2 by means of a first hinge 32a.

In detail, the intermediate component 30, or better the proximal end 30a thereof, is inserted into the intercondylar space 10 of the femoral component 2. Subsequently, the pin 150 is inserted into the through hole 15 present in the femoral component 2 and into the through hole 31a of the proximal end 30a of the intermediate component 30.

Figure 13:
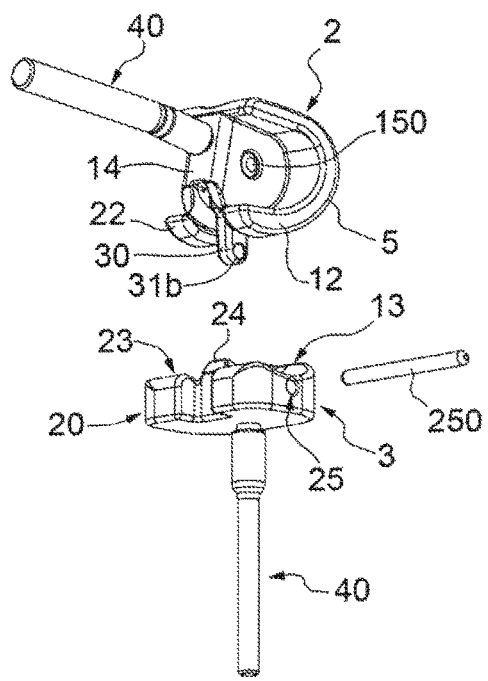
FIG. 13 is a side perspective view of the constrained prosthesis according to the present invention during an implantation or assembly step.

In one version of the invention, the intermediate element 30 leaves the factory already inserted into the intercondylar space 10 of the femoral component 2 and already fixed with the pin 150 (as illustrated in FIG. 13).

The doctor at this point may apply the additional shank 40, if necessary, and possibly orient the same with respect to the femoral bone F, and then insert the femoral component 2 into the femur F after cementing the bone stumps.

At this point, the doctor prepares the tibial component 3 applying the additional shank 40 or not and orienting it with respect to the tibial bone P, if necessary; he then inserts the tibial component 3 into the tibia P, always after interposing some cement for fixing the component itself on the bone.

The doctor, then, brings the femur F and the tibia P close together, and then the femoral component 2 and the tibial component 3.

The method thus provides for inserting the intermediate component 30 into the tibial component 3 and constraining the intermediate component 30 to the tibial component 3 by means of a second hinge 32b.

In this manner, the distal end 30b of the intermediate component 30 is then inserted into the opening or recess 18 of the tibial component 3.

The pin 250 is inserted into the second hinge 32b or, in detail, into the opening 25 of the tibial component and passes through the through hole 31b of the distal end 30b of the tibial component 30.

In this way, the pins 150, 250 constitute the hinges 32a and 32b of the constrained prosthesis 1 of the present invention.

After inserting the pin 250 into the hinge 32b, the method provides for cementing the pin 250 into the second hinge 32b; the doctor, then, may obstruct the orifices thereof with some cement in order to ensure the removability thereof.

If necessary, as mentioned, the additional shanks 40 are fixed to the cylindrical protrusion or shank 16 of the femoral component and/or of the tibial component.

Once assembled, or during implantation, the constrained prosthesis 1, its various components and/or the additional shanks 40 may be oriented so as to adapt in the best way possible to the dimensions and the anatomy of the patient or the specific needs of the implant.

If, for any reason, the doctor will have to remove the constrained prosthesis 1 after the implantation, he will perform in reverse order the steps used for its assembly and mentioned above. Therefore, after having opened a surgical way, for example by means of a metal punch or other tool, he will push the pin 250 out of its seat. Such operation will be easy as the cement placed to block the pin 250 itself will easily break.

The patient's knee will then be bent over 90° and the doctor will be able to extract the tibial component 3 and subsequently the femoral component 2. It is thus clear how the second function of the intermediate component 30 is that of facilitating and assisting both the assembly or the implantation of the two components 2, 3 of the constrained prosthesis 1 and their subsequent removal.

As seen, the constrained prosthesis 1 satisfies the above described advantages in that, while being implanted both in situations of severe bone loss and loosening of the ligaments and in less damaged situations, it is constrained, thereby ensuring a good stability to the knee joint.

Moreover, due to the presence of the two hinges 32a and 32b, the movement performed by the joint—which comprises both rolling and translating of the femoral component 2 on the tibial component 3—is more consistent with that anatomically performed under non-pathological normal conditions.

Moreover, thanks to this, the patient can lead a self-sufficient life for the whole period of use of the constrained prosthesis according to the present invention.

The constrained prosthesis 1 according to the present invention is made of biologically compatible material.

Such biologically compatible material may be chosen from metals, metal alloys, organo-metallic compounds. Such materials may comprise inserts of polymer material, such as for example polyethylene.

In one version of the present invention, the biologically compatible material may comprise or be coated with an acrylic resin or a plastic material, a ceramic material, or a highly porous resin, and/or a combination thereof or a bone cement, for example polymethylmethacrylate (PMMA), or in which the aforesaid plastic materials may be chosen from thermoplastic polymers, such as acrylic resins, polyethylene, polypropylene, polyester, thermoformable polymers and other similar materials.

The constrained prosthesis 1 may comprise a metal core capable of conferring a better stability to the implant, a high load resistance, etc.

Such metal core is necessary since the prosthesis 1, which must be articulated in a constrained manner, requires a rigid reinforcement structure capable of resisting the mechanical stresses caused by the mechanical constraint.

In one version of the invention, the constrained prosthesis 1 has the inner core—as a reinforcement structure—made of metal and/or as a combination of different plastic materials such as PMMA (polymethylmethacrylate) and UHMWPE (ultra-high-molecular-weight polyethylene).

In particular, the pins 150, 250, constituting the hinges 32a and 32b, must be inserted into holes reinforced by the metal core, in order to support the loads that are concentrated in such areas.

The pins 150, 250 may be made of a metal material, such as for example steel, possibly coated with biologically compatible material, such as plastic material or bone cement.

Such metal core, in one version of the invention, is present both inside the femoral component 2, and the tibial component 3 and also the intermediate component 30.

Such metal core may not be required since the constrained prosthesis 1 is already made of metal material.

The cylindrical protrusions or shanks 16 are made of metal material, possibly coated with the aforesaid biologically compatible material, such as plastic material or bone cement.

Figure 5:
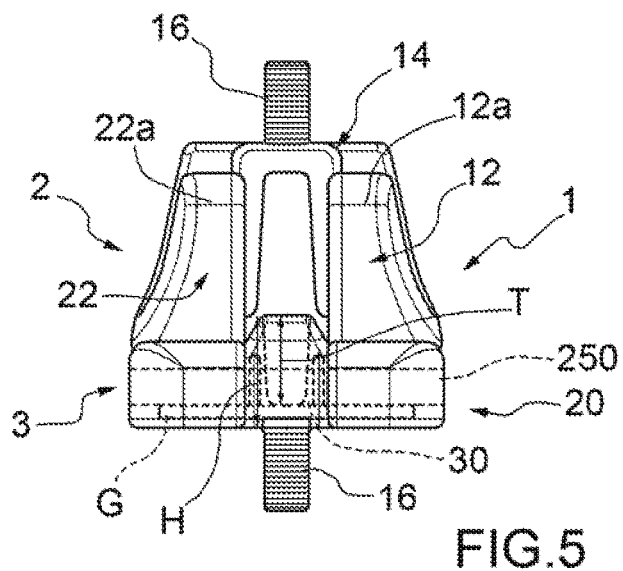
FIG. 5 is a rear view of the assembled constrained prosthesis according to the present invention.
Figure 6:
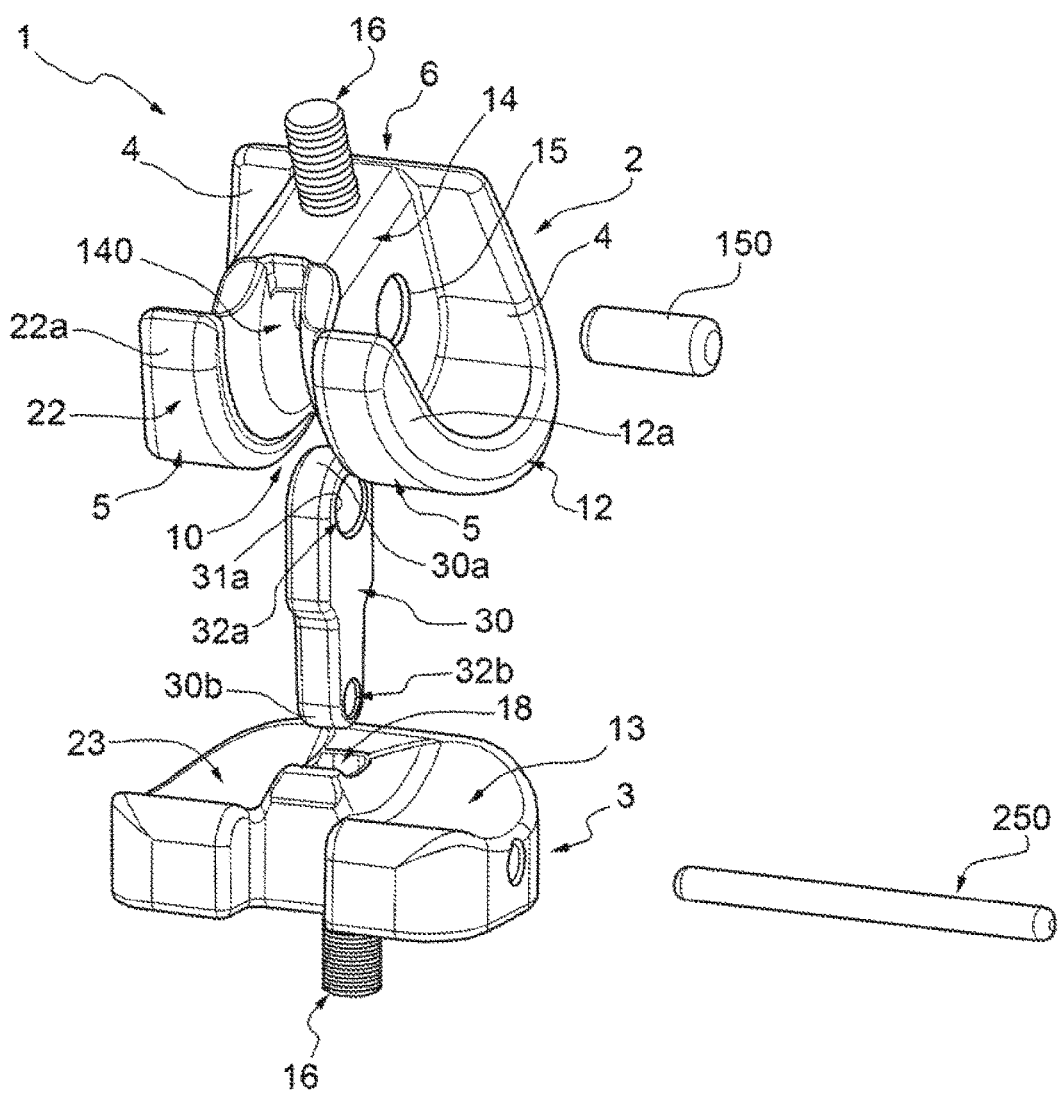
FIG. 6 is an exploded perspective rear-side view of the constrained prosthesis of FIG. 5.

In a specific version of the invention, illustrated by way of example in the FIGS. 5 and 7, the constrained prosthesis 1 and/or at least the tibial component 3 thereof, comprise a metal core G, coated with bone cement.

In a further version of the invention, the constrained prosthesis 1 is made of PMMA or the metal core G is coated with PMMA.

The femoral component 2 and the tibial component 3 are preformed.

The biologically compatible material of the constrained prosthesis 1 may be porous.

The invention thus conceived is susceptible of numerous modifications and variants, all falling within the scope of the inventive concept.

In addition, all details can be substituted by other technically equivalent elements. In practice, the materials used, as well as the contingent shapes and sizes, can be of any type in accordance with the requirements, without departing from the protective scope of the following claims.

The invention claimed is:

1. A method for assembling a constrained prosthesis for the knee joint comprising a femoral component, a tibial component and an intermediate component, wherein said femoral component comprises a first condylar portion and a second condylar portion, each respectively comprising a first and a second posterior portion, wherein the first and second posterior portions are separated from each other by an intercondylar space, said first condylar portion being placed laterally and said second condylar portion being placed medially with respect to the sagittal plane of the human body, wherein said femoral component is adapted to be constrained to an end of the femoral bone in proximity to the knee joint, wherein said tibial component is adapted to be constrained to an end of the tibial bone in proximity to the knee joint, wherein said intermediate component has a proximal end placed at said femoral component and a distal end placed at said tibial component, wherein said proximal end has a through hole and wherein said distal end has a through hole, said femoral component being suitable for coming into contact and articulating with said tibial component, wherein said tibial component comprises a tibial plateau, said tibial plateau comprising two condylar articular bases, corresponding to said condylar portions, and an intercondylar protuberance placed between said condylar articular bases and suitable, in use, for being inserted into the intercondylar space of said femoral component, said intercondylar protuberance has an opening or recess extending substantially parallel with respect to the longitudinal axis of the human body, said opening or recess extending inside said tibial component for a certain length (T), comprising the steps of:

associating said intermediate component in a constrained manner with said femoral component through a first hinge, inserting said intermediate component into said tibial component, wherein said step of inserting said intermediate component in said tibial component includes inserting, in use, said distal end of said intermediate component into said opening or recess, so as to allow said distal end to move at least in the sagittal direction in said opening or recess, constraining said intermediate component to said tibial component through a second hinge, said first hinge and said second hinge being suitable for rotatably constraining said femoral component to said tibial component.

2. The method according to claim 1, wherein said step of associating in a constrained manner said intermediate component with said femoral component through a first hinge comprises inserting a proximal end of said intermediate component into the intercondylar space of said femoral component and inserting a pin into said first hinge.

3. The method according to claim 2, wherein said step of constraining said intermediate component to said tibial component through a second hinge comprises inserting a pin into said second hinge.

4. The method according to claim 1, further comprising a step of cementing said pin in said second hinge.

5. The method according to claim 1, comprising a step of associating to said tibial component and/or to said femoral component at least one additional shank or a ring or a thickness, adapted, in use, to elongate the bone ends of the patient and/or to orient said tibial component and/or said femoral component with respect to the bone ends of the patient.

* * * * *